US007229595B2

(12) United States Patent
Richardson et al.

(10) Patent No.: US 7,229,595 B2
(45) Date of Patent: Jun. 12, 2007

(54) FILTRATION COLUMN DEVICES AND METHODS OF FILTERING THEREWITH

(75) Inventors: Derrick A. Richardson, Pembroke, FL (US); Derek S. Pai, Redwood City, CA (US); Jorge Monteon, San Jose, CA (US)

(73) Assignee: Molecular Devices Corporation, Sunnyvale, CA (US)

( * ) Notice: Subject to any disclaimer, the term of this patent is extended or adjusted under 35 U.S.C. 154(b) by 0 days.

(21) Appl. No.: 09/882,530

(22) Filed: Jun. 15, 2001

(65) Prior Publication Data
US 2002/0192656 A1    Dec. 19, 2002

(51) Int. Cl.
*B01L 11/00*    (2006.01)
*B32B 5/02*    (2006.01)
*B32B 27/04*    (2006.01)
*B32B 27/12*    (2006.01)
*C07H 21/00*    (2006.01)
*C07H 21/02*    (2006.01)
*C07H 21/04*    (2006.01)

(52) U.S. Cl. ............... 422/101; 422/69; 422/70; 422/100; 422/102; 536/25.4; 536/124; 536/127

(58) Field of Classification Search ........... 210/656; 536/22.1, 23.1, 124, 127, 25.4; 422/69, 70, 422/100, 101, 102
See application file for complete search history.

(56) References Cited

U.S. PATENT DOCUMENTS

| | | | |
|---|---|---|---|
| 3,917,458 A * | 11/1975 | Polak ........................ 23/262 |
| 4,214,993 A | 7/1980 | Forsythe, Jr. et al. |
| 4,320,769 A | 3/1982 | Eichhorn et al. |
| 4,485,015 A | 11/1984 | Smith |
| 4,683,058 A * | 7/1987 | Lyman et al. ............... 210/359 |
| 4,920,053 A | 4/1990 | Inoue et al. |
| 5,057,426 A | 10/1991 | Henco et al. |
| 5,075,430 A | 12/1991 | Little |
| 5,103,338 A | 4/1992 | Crowley et al. |
| 5,192,503 A | 3/1993 | McGrath et al. |
| 5,234,809 A | 8/1993 | Boom et al. |
| 5,246,866 A | 9/1993 | Nasu et al. |
| 5,280,384 A | 1/1994 | Shibasaki |
| 5,438,128 A | 8/1995 | Nieuwkerk et al. |
| 5,494,646 A | 2/1996 | Seymour |
| 5,496,523 A | 3/1996 | Gazit et al. |
| 5,504,366 A | 4/1996 | Weiss et al. |
| 5,513,768 A | 5/1996 | Smith |
| 5,532,128 A | 7/1996 | Eggers et al. |
| 5,538,849 A | 7/1996 | Uematsu et al. |
| 5,545,531 A | 8/1996 | Rava et al. |
| 5,559,329 A | 9/1996 | Joseph et al. |
| 5,619,035 A | 4/1997 | Weiss et al. |
| 5,639,428 A | 6/1997 | Cottingham |
| 5,652,141 A | 7/1997 | Henco et al. |
| 5,677,197 A | 10/1997 | Gordon et al. |
| 5,722,553 A | 3/1998 | Hovatter |
| 5,756,049 A | 5/1998 | Brayton |
| 5,798,215 A | 8/1998 | Cathey et al. |
| 5,808,041 A * | 9/1998 | Padhye et al. ............. 536/25.4 |
| 5,843,644 A | 12/1998 | Liotta et al. |
| 5,843,767 A | 12/1998 | Beattie |
| 5,859,699 A | 1/1999 | Baer et al. |
| 5,860,937 A | 1/1999 | Cohen |
| 5,874,219 A | 2/1999 | Rava et al. |
| 5,879,625 A | 3/1999 | Roslaniec et al. |
| 5,891,630 A | 4/1999 | Eggers et al. |
| 5,910,246 A | 6/1999 | Walter et al. |
| 5,985,085 A | 11/1999 | Baer et al. |
| 6,020,186 A | 2/2000 | Henco et al. |
| 6,103,195 A | 8/2000 | Shukla et al. |
| 6,157,446 A | 12/2000 | Baer et al. |
| 6,177,278 B1 * | 1/2001 | Ha-Ahmad .................. 436/94 |
| 6,204,030 B1 | 3/2001 | Liotta et al. |
| 6,218,531 B1 | 4/2001 | Ekenberg |
| 6,277,648 B1 | 8/2001 | Colpan |

FOREIGN PATENT DOCUMENTS

| WO | WO 93/11221 | 6/1993 |
|---|---|---|
| WO | WO 95/23960 | 9/1995 |
| WO | WO 96/40435 | 12/1996 |

(Continued)

OTHER PUBLICATIONS

Bio-Rad, Life Science Products Catalog (1993), pp. 57 and 60-63.*

(Continued)

*Primary Examiner*—Patrick T. Lewis
(74) *Attorney, Agent, or Firm*—Fish & Richardson P.C.

(57) ABSTRACT

This relates to filter columns for isolating nucleic acids. The filter column is adapted for stable placement within the upper portion of standard plastic collection tubes of various sizes. The body of the filter column has a number of surfaces to accommodate placement within variously sized collection tubes. The filter column contains nucleic acid-specific filter which can be located at alternate regions within the filter column, providing different filter surface areas and loading volume capacities using the same column body. The filter column has an opening on an upper end adapted to be sealed by a cap. A method for recovering nucleic acids using such filter column is also provided.

26 Claims, 8 Drawing Sheets

FOREIGN PATENT DOCUMENTS

| | | |
|---|---|---|
| WO | WO 97/13838 | 4/1997 |
| WO | WO 98/11989 | 3/1998 |
| WO | WO 98/35215 | 8/1998 |
| WO | WO 98/42874 | 10/1998 |
| WO | WO 99/17094 | 4/1999 |

OTHER PUBLICATIONS

U.S. Appl. No. 08/984,979, filed Dec. 4, 1997, Baer et al.
U.S. Appl. No. 09/018,452, filed Feb. 4, 1998, Baer et al.
U.S. Appl. No. 09/058,711, filed Apr. 10, 1998, Baer et al.
U.S. Appl. No. 09/121,635, filed Jul. 23, 1998, Baer et al.
U.S. Appl. No. 09/121,677, filed Jul. 23, 1998, Baer et al.
U.S. Appl. No. 09/121,691, filed Jul. 23, 1998, Baer et al.
U.S. Appl. No. 09/208,604, filed Dec. 8, 1998, Baer et al.
U.S. Appl. No. 09/562,495, filed May 1, 2000, Lossing et al.
U.S. Appl. No. 09/617,742, filed Jul. 17, 1997, Baier et al.
Bonner, R. F. et al. (1997). "Laser Capture Microdissection: Molecular Analysis of Tissue," *Science* 278:1481-1482.
Brignole, E. (2000). "Laser-Capture Microdissection," pp. 1-4, located at <<http://pubs.acs.org/subscribe/journals/mdd/v03/i09/html/toolbox.html>> from *Modern Drug Discovery*, 3(9):60-70.
Chu, S. S. et al. (2000). "Laser Capture Microdissection: Applications in Cancer Research," *Cancer Research* pp. 1-4.
Chui, G. (1999). "The Ecosystems Within" Section F, Science & Technology *San Jose Mercury News* pp. 1-5.
Emmert-Buck, M. R. et al. (1996). "Laser Capture Microdissection," *Science* 274:998-1001.
Goldsworthy, S. M. et al. (1999). "Effects of Fixation on RNA Extraction and Amplification from Laser Capture Microdissected Tissue" *Molecular Carcinogenesis* 25:86-91.
Isenberg, G. et al. (1976). "Cell Surgery by Laser Micro-Dissection: a Preparative Method," *Journal of Microscopy* 107:19-24.
Meier-Ruge, W. et al. (1976). "The Laser in the Lowry Technique for Microdissection of Freeze-Dried Tissue Slices," *Histochemical Journal* 8:387-401.
Relman, David A. (1999). "The Search for Unrecognized Pathogens," *Science* 284:1-3.
Schindler, M. et al. (1985). "Automated Analysis & Survival Selection of Anchorage-Dependent Cells Under Normal Growth Conditions," *Cytometry* 6(4):368-374.
Schindler, M. (1998). "Select, Microdissect & Eject," *Nature Biotechnology* 16:719-720.
Schütze, K. and Lahr, G. (1998). "Identification of expressed genes by laser-mediated manipulation of single cells," *Nature Biotechnology* 16(8):737-742.
Simone, N. et al. (1998). "Laser Capture Microdissection; Opening the Microscopic Frontier to Molecular Analysis," *Trends Genet.* 14(7):272-276.

* cited by examiner

FILTRATION COLUMN DEVICES AND METHODS OF FILTERING THEREWITH

FIELD OF THE INVENTION

This invention relates to filtration filter columns and methods of filtering therewith. More specifically, this invention relates to system and methods for isolating nucleic acids such as ribonucleic acid (RNA) and deoxyribonucleic acid (DNA) from other materials such as enzymes, salts, buffers, small molecules, and cellular debris.

BACKGROUND OF THE INVENTION

Isolation and purification of nucleic acids play a central role in modern molecular biology, and increasingly in medicine. Both laboratory and diagnostic research require the use of nucleic acids in gene cloning and genetic analysis. Many of these techniques require keeping ribonucleic acid (RNA) or deoxyribonucleic acid (DNA) pure and free of contamination. In many instances, the availability of small amounts of starting sample material poses a problem during isolation of the nucleic acid. The limited amount of sample material makes the need to limit loss of the sample material a critical concern.

A known method for isolating nucleic acids from a small amount of starting material includes the use of a spin filter column ("filter column") that contains a nucleic acid binding material (i.e., a filter). Examples of binding material/filters include silicas like glass powder, silica particles, glass microfibers, diatomaceous earth, etc. These filters are often associated with a "filter surface area." This filter surface area is not limited to the surface area of a side of the filter. Instead, since the filters are usually comprised of microscopic fibers, particles, porous substances, etc., the filter surface area is actually defined by the surface area of the components which comprise the filter. For example, a filter that comprises glass microfibers may have a filter surface area defined by the surface area of the microfibers within the filter (either all of the microfibers or a portion thereof).

In some cases, filter columns may isolate nucleic acids directly from cells or biological tissue. In the first step a filter column is inserted into a microcentrifuge tube (e.g., a 1.5 ml tube) and a solution containing nucleic acids along with undesirable impurities is loaded into the top of the filter column. Depending upon the application, the starting material containing the nucleic acids is prepared from cells that have been treated with a disrupting solution causing the release of the nucleic acids. Alternatively, the nucleic acid solution is the product of an earlier reaction step. In either case, the nucleic acid binds to the filter column filter in the presence of a chaotropic agent. Then the filter column is centrifuged in a microcentrifuge. Centrifugation forces the solution through the filter column's filter and binds the nucleic acid to the filter. Next, the filter with the nucleic acids bound therein is washed by applying a washing solution to the top of the filter column, and centrifuging again. After each wash the filter column can be removed from the collection tube so that the collection tube may be emptied. Finally, placement of an elution buffer (usually water having a specific pH) at the top of the column and applying centrifugation elutes the nucleic acid that is bound to the filter. Given the proper pH, the nucleic acid elutes into the liquid, and then collects into the collection tube. It is important to note that the volumes of the binding and wash solutions can be relatively large, thus necessitating the use of a larger (1.5-2.0 mL) tube. On the other hand, the volumes for elution are often smaller, making it desirable to have a smaller tube for the elution step. Eluting directly into a smaller tube allows one to proceed to the next reaction step in the small tube, rather than having to pipette out of the large tube. As discussed herein, use of a pipette is undesirable as it introduces the risk of loss of samples as well as contamination of the sample. Moreover, as described herein, there are additional benefits in keeping the sample solution in a smaller tube.

Several companies provide kits that include filter columns designed to use this technique for isolating nucleic acids. QIAGEN, Promega, and Boehringer Mannheim GmbH offer filter columns based on the above described principle. However, existing filter columns cannot be used interchangeably with collection tubes of different sizes. Instead, these previously known filter columns only fit into a single size collection tube (e.g., a standard 1.5-2.0 mL microcentrifuge tube.)

This limitation presents a problem as many applications may benefit if a single filter column could be interchanged with collection tubes of multiple sizes. For example, given a small amount of nucleic acid in the starting material, it is best to elute the purified nucleic acid into a very small volume of fluid so that nucleic acid does not become too dilute in the fluid. Obviously, the resulting combination of elution buffer and nucleic acid will occupy a small volume. Many applications that require processing of nucleic acid may benefit when storing this small volume of material in a smaller sized collection tube. For instance, an application such as amplification of the purified DNA by polymerase chain reaction (PCR) requires placement of the nucleic acid into a thin-walled 0.5 mL or 0.2 mL microcentrifuge tube.

Accordingly, it may seem ideal to use a smaller filter column which is specifically designed to fit a 0.5 mL or 0.2 mL microcentrifuge tube. However, a significant drawback is that these smaller filter columns limit the amount of wash solution that can be passed through the column with each wash. This limitation necessitates additional wash steps and increased handling of the filter column and microcentrifuge tube, thus presenting an undesirable increased risk of contamination. Also, as discussed above, the requirement of large volumes of binding and wash solutions often necessitate the use of a larger collection tubes (e.g., a 1.5-2.0 mL microcentrifuge tube.)

The remaining alternative is to use a filter column specifically designed to fit into a larger collection tube (e.g., a 1.5 mL-2.0 microcentrifuge tube.) While this alternative minimizes the additional wash steps and increased handling discussed above, the alternative presents additional problems. For instance, after purification, the nucleic acid solution must be eluted from the filter column into an appropriately sized 1.5 mL-2.0 mL microcentrifuge tube. As discussed above, many applications may benefit by storing the elution buffer and nucleic acid in a smaller sized microcentrifuge tube. Consequently, the elution buffer and nucleic acid must then be transferred (e.g., by aspiration) into a smaller (e.g. 0.5 mL) tube. Again, this extra transfer step introduces the undesirable potentials of contamination and loss of some of the nucleic acid.

In view of the above, there remains a need to use different-sized collection tubes with a single filter column. The ability to use different-sized collection tubes with a single filter column overcomes the problems associated with the existing art.

The invention described herein addresses the problems discussed above. Moreover, the invention described herein allows centrifugation from one filter column into at least two distinct sizes of collection tubes. The disclosed invention may be used with commercially available collection tubes.

SUMMARY OF THE INVENTION

This invention relates to filtration filter column devices and methods of filtering therewith. The invention includes a filter column filter which has a plurality of bearing surfaces along with a plurality of body portions of varying outer diameters each of which is adapted to seat on respective collection tubes of different sizes.

A variation of the invention includes a lid which may be either discrete from the filter column or may be integral with the filter column body. In the latter case, the lid may be joined to the filter column body by a hinge or other member.

A variation of the invention includes a filter column which contains vents within a passageway of the filter column. The vents permit placement of a lid on the filter column without increasing the pressure within the passageway thereby causing sample material to be forced out of the filter column.

Another variation of the invention includes deformable ribs which may be placed about an outer surface of the filter column. Such deformable ribs may assist placement of the filter column within closely varying sizes of collection tubes.

The invention includes kits for isolation of nucleic acid from a solution containing nucleic acids and contaminating material The kit contains the filter column, collection tubes, binding buffer, wash solutions and elution buffer.

The invention includes a method of providing a biological material containing a nucleic acid material in a single filter column having a filter, where the filter column has a plurality of surfaces permitting the filter column to be secured within at least two collection tubes of different sizes, fitting the filter column into a first collection tube, transferring the solution containing nucleic acid to the filter of the filter column in the presence of an agent capable of promoting binding of the nucleic acid material to the filter, transferring the flow-through solution from the filter column to the first collection tube via centrifugal force, washing the filter column filter with a wash solution, removing the filter column from the first collection tube and eluting the nucleic acid material from the filter column filter, by placing the filter column in a second collection tube and applying centrifugal force.

DETAILED DESCRIPTION OF THE INVENTION

The following discussion of the variations of the invention and the reference to the attached drawings are for explanatory purposes and do not exhaustively represent the possible combinations and variations of the invention. Those skilled in the art will readily appreciate that many variations may be derived using the following description. The following examples are intended to convey certain principles of the invention. These examples are not intended to limit the scope of the claims to any particular example. It is understood that the claims are to be given their broadest reasonable interpretation in view of the description herein, any prior art, and the knowledge of those of ordinary skill in the field.

Figure 1A:
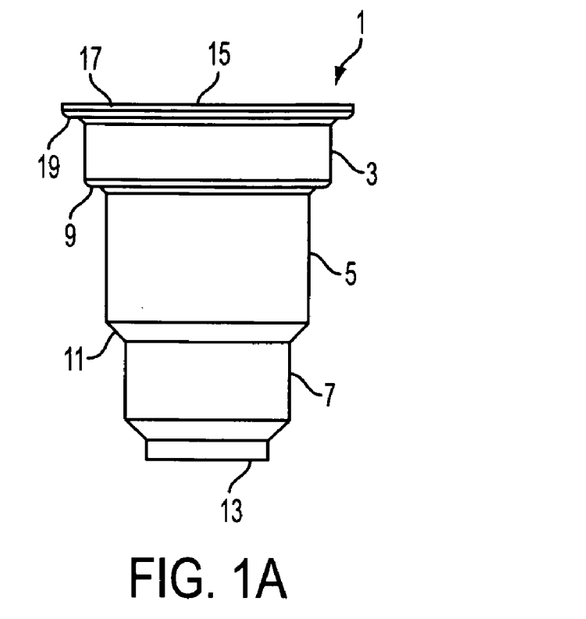
FIGS. 1A and 1B illustrate variations of filter columns of the present invention appropriate for mating with collection tubes of varying sizes.
Figure 1B:
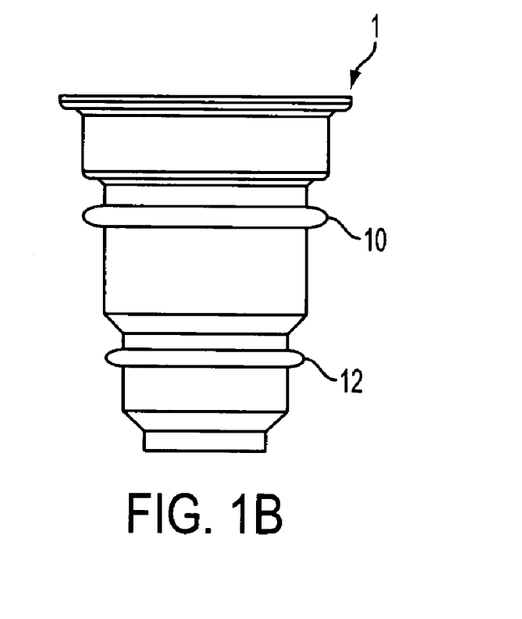

FIG. 1A shows a profile of a variation of the present invention. In this variation, the filter column 1 includes a first body portion 3, a second body portion 5, and a third body portion 7. The filter column 1 also contains a first bearing surface 9 and a second bearing surface 11 located between body portions 3, 5, 7 as illustrated. The bearing surfaces are intended to permit placement of the filter column 1 in various collection tubes (e.g., see FIGS. 4 and 5.) Accordingly, the present invention contemplates that the bearing surfaces, either alone, or along with body portion(s) adjacent to a bearing surface, serve to provide stability of a filter column within a collection tube. Such stable placement being necessary for the intended use of the filter column (e.g., during centrifugation, vacuum filtering, handling, adding/removing material, etc.) Furthermore, although bearing surfaces 9, 11 are located at the intersection of the respective body portions, in other variations of the invention the bearing surfaces may be located anywhere along the various body portion. As illustrated in FIG. 1B where the bearing surfaces 10, 12, are located along respective body portions of a filter column 1. Additionally, while bearing surfaces 9, 11, are illustrated as being tapered, the invention is not limited as such.

Variations of the invention also include filter columns with more than three body portions. The variation of the spin-column depicted in FIG. 1 further includes an outer rim 17 adjacent to a top 15 of the filter column 1. The outer rim 17 may also provide an additional bearing surface 19 and may also aid in grasping and manipulating the filter column 1. The bottom of the filter column may be reduced in diameter 13 to assist in retaining a filter (not shown) within the filter column 1.

It is noted that the body of the filter column may be adapted as required to accommodate any particular filtration process for example, centrifugation, vacuum filtering, or any known filtering process. For example, if a filter column of the present invention is intended for use with vacuum filtering, the filter column may also include a manifold to accommodate the vacuum. Such modifications are well known to those familiar with filter columns and methods of using such devices.

The dimensions of the body portions 3, 7 are selected so that the filter column 1 may fit into various collection tubes that are sized for the respective body portion and bearing surface. Variations of the invention include sizing of a filter column to include body portions and bearing surfaces that accommodate both a 1.5-2.0 mL and a 0.5 mL microcentrifuge tube. An example of such tubes includes PGC Scientifics No. 16-8105-52 (1.5 mL) supplied by PGC Scientifics Corporation of Maryland, Eppendorf No. 22 36 430-8 (0.5 mL) supplied by Eppendorf AG of Germany, and Gene Amp No. N801-0611 (0.5 mL) supplied by Perkin-Elmer Life Science of Massachusetts. For example, the opening diameter for a 1.5 mL-2.0 mL microcentrifuge tube may range from 0.32-0.37 in. The opening diameter for a 0.5 mL microcentrifuge tube may range from 0.26-0.27 in. It is intended that, where appropriate, the definition of diameter of the filter column may includes any such external feature as crush ribs, buttress, collar, or any other feature that may be present on a portion of a filter column body that is intended for insertion into a collection tube.

While the invention may be suited for use with the tubes described above, the invention is not limited to compatibility with such tubes. Moreover, although variations of the inventive device described herein are discussed for use with existing microcentrifuge tubes ranging in size from 0.5 mL capacity to 1.5-1.5 mL capacity, the invention is not limited as such. Instead, the inventive device may be applied to collection tubes as described herein, centrifuge tubes of any size, or any type of collection tube where a benefit from the improvements of the current invention are desirable. Furthermore, the invention may be adapted to accommodate any number of combinations of large and small collection tubes, including, but not limited to a filter column adapted to accommodate a large 0.5 mL tube and a small 0.2 mL tube, or a filter column adapted to accommodate a large 1.5 mL tube and a small 0.2 mL tube.

The height of the filter columns of the present invention is selected so that the filter column along with the particular collection tube used will fit within the centrifuge apparatus (e.g., an Eppendorf 5415C centrifuge supplied by Eppendorf AG of Germany.) For example, for a 0.5 mL microcentrifuge tube to fit in the centrifuge previously listed, the height which protrudes from the 0.5 mL microcentrifuge tube (i.e., referring to FIG. 1A, the height from the top of bearing surface 11 to the top of the device) must be below 0.625 in. preferably below 0.5 in.

The filter columns of the present invention may be fabricated from materials readily known to those familiar with existing filter columns. Such materials include, but are not limited to, polypropylene or polycarbonate. Polyethylene, Fluoropolymers such as polytetrafluoroethylene and polyvinylidine flouride, Polyarylene ether ketones, and copolymers. It is often desirable to use a material which is thermoplastic to allow molding of the columns. The columns can also be machined out of appropriate materials. In some cases, it is desirable to choose materials which permit sterilization of the filter column thereby allowing the filter column, filter, and sample to be nuclease-free.

Figure 2:
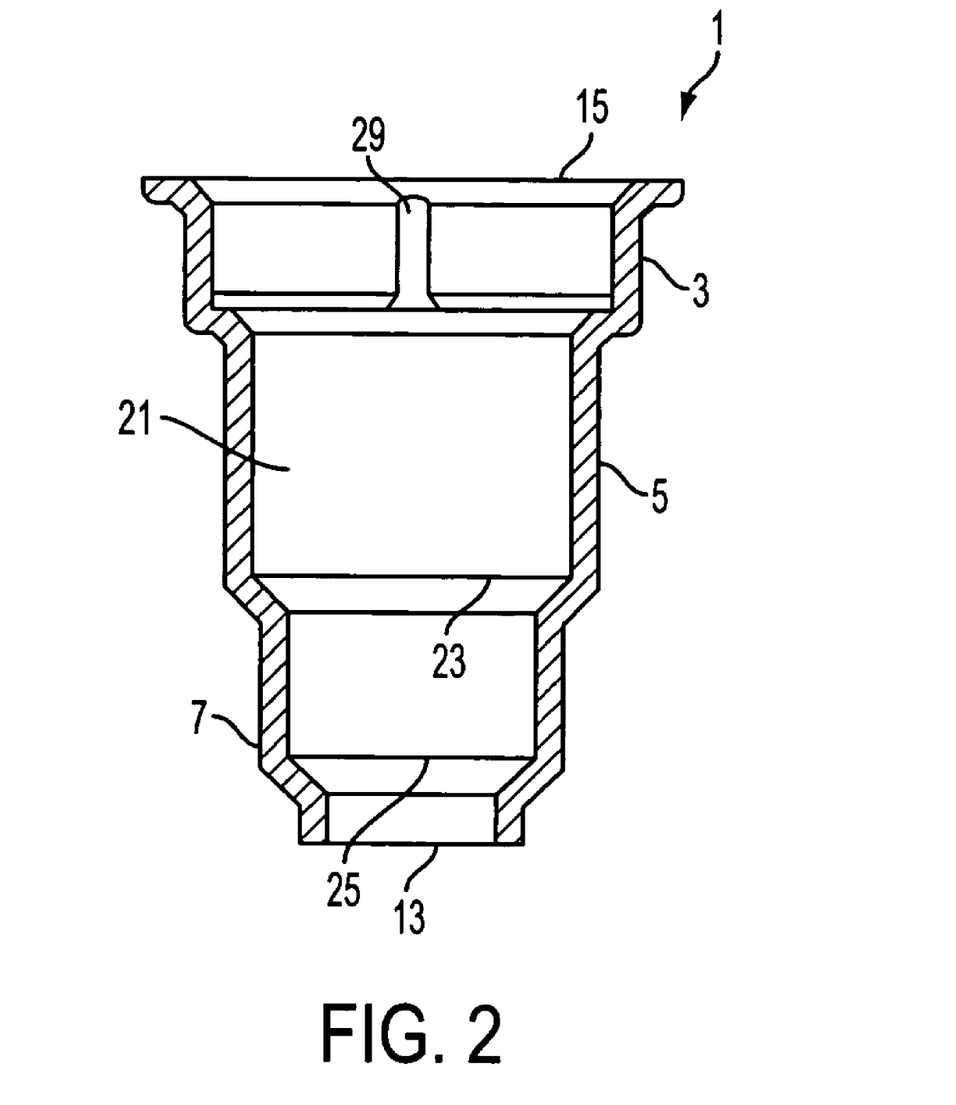
FIG. 2 illustrates a sectional view of a variation according to the invention.

FIG. 2 illustrates the internal body structure of a variation of a filter column of the present invention. Liquid solutions may be loaded into the top of the filter column 15. Typically, liquid solutions include the nucleotide-containing solution, wash or rinsing solutions and an elution buffer (water or TE). The nucleic acid solution can be from a lysate (e.g. isolated directly from cells), or nucleic acids from a reaction mixture. The nucleic acids from reaction mixtures could be from reactions such as PCR, DNA or RNA polymerization, reverse transcription, etc. Before being loaded onto the filter column the nucleic acid solution is usually combined with a binding buffer containing a chaotropic agent to aid in binding the nucleic acid to the filter. The compositions of binding buffers, wash or rinsing solutions and elution buffer is well known in the field and can be found in U.S. Pat. Nos. 5,075,430 to Little, 5,808,041 to Padhye, and 5,652,141 to Henco, the entirety of each of which is hereby incorporated by reference.

The variation of the invention depicted in FIG. 2 also illustrates a vent 29. The vent 29 may be located along an interior surface of a passageway 21 of a filter column 1 but will be placed in fluid communication with an exterior of the filter column 1. The vent 29 permits venting of pressure within the passageway 21 during placement of a lid (not shown) in the top opening 15 of the filter column 1. Without a vent, the placement of a lid could increase pressure within the passageway 21 such that sample material is forced out of the bottom 13 of the filter column 1. Although such displacement of the material may not have an effect on the function of a device of the present invention, such an occurrence may be undesirable. It is contemplated that the device 1 may have any number of vents. These vents may be placed randomly or spaced evenly apart on a wall of a passageway. In one variation (not shown) four vents are placed at intervals of 90° along the walls of the passageway. It is further contemplated that a vent may be placed in another location in the filter column 1 or even within a lid (not shown) itself.

As illustrated in FIG. 2, the filter column 1 of the present invention also allows for varying placement of a filter (not shown) within a passageway 21 of the filter column 1. For example, placement of a filter in a bottom 23 of the second body portion 5 permits the filter column 1 to provide a certain volume capacity. The volume capacity of the filter column 1 can increase by changing the location of the filter to a bottom 25 of the third body portion 7. Accordingly, the same filter column 1 body may be used for varying application. To maximize the volume of fluid that can be added to a filter column of the present invention, a filter can be located in the lowest chamber. Moreover, locating the filter towards a middle chamber reduces the volume of fluid that may be added but permit a larger filter surface area as the diameter of the middle chamber may be greater than the diameter of a lower chamber. For the filter, it is desirable to have a high surface area fiber glass filter, (e.g., a borosilicate glass). The filter may be one that is adapted to isolate nucleic acids from a liquid sample by, for example, centrifugation, vacuum filtering, or any other filtering method. Surface area refers to the total surface area of all the fibers and not just the area of the disk. The total surface area may range between 1,000 $mm^2$ and 50,000 $mm^2$. Moreover, filter columns of the present invention may have a microliter capacity greater than 200 microliters. Another variation of the filter column having a microliter capacity ranging between 50 microliters and 1000 microliters. The microliter capacity is defined by the volume within a passageway of the filter column that above the filter.

Figure 3:
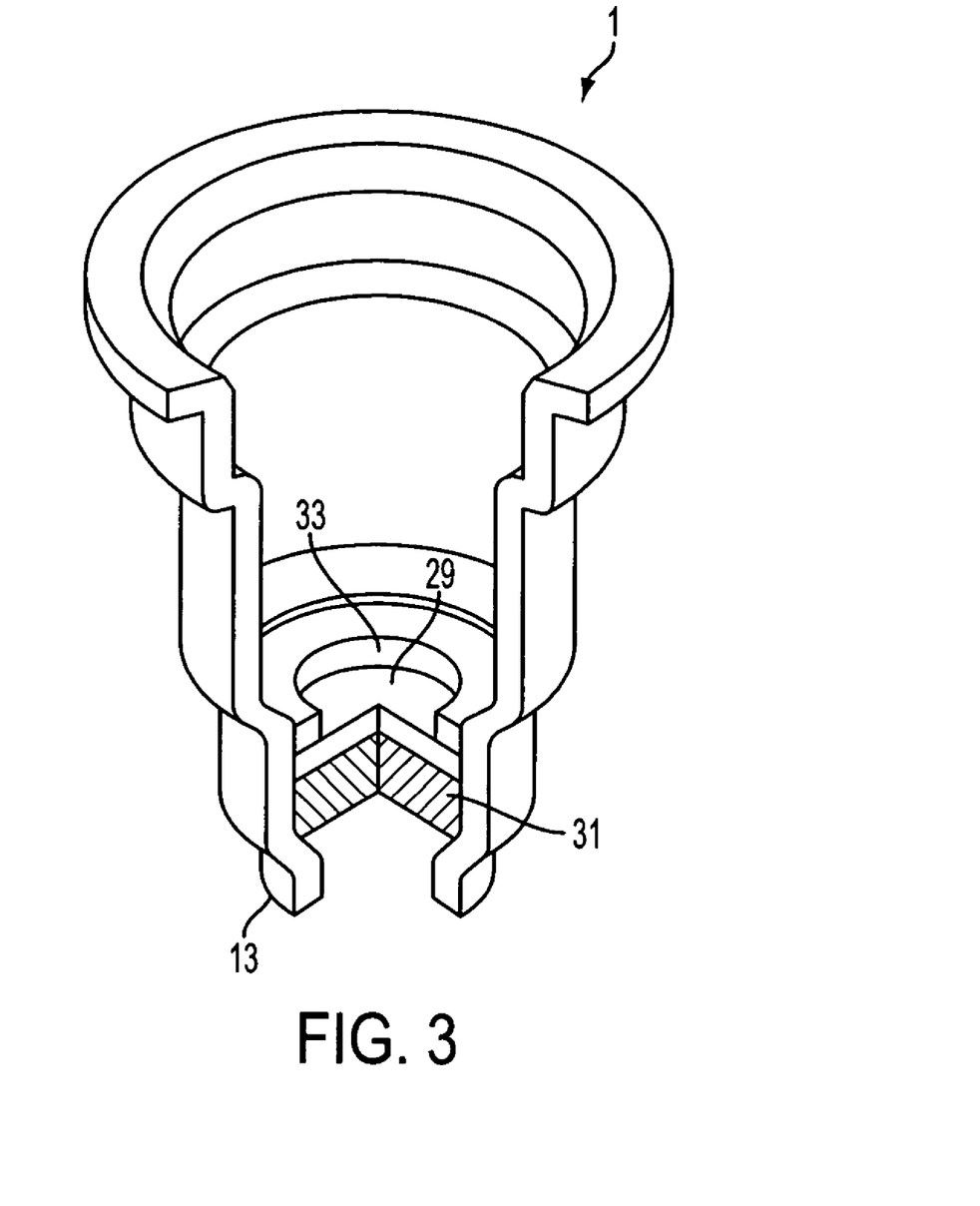
FIG. 3 illustrates a cut-away profile view of a variation of a filter column of the present invention containing a filter.

Securing of the filter may be accomplished, for example, by placement of a disk of porous substrate material (not shown) at position 25. A filter membrane (not shown) is placed on top of the substrate material. Optionally, a retaining ring (not shown) is added such that there is an interference between the retaining ring and the wall of the passageway. Accordingly, the retaining ring secures the filter on the porous substrate. Another means of securing the filter is to mold an integral grating within the passageway to seat the filter. FIG. 3 illustrates placement of a filter using the porous substrate and retaining ring.

FIG. 3 illustrates a cut-away profile view of a variation of a filter column 1 of the present invention. The illustration shows a filter 29 held in the lower portion of the filter column 1. In this variation, the filter 29 is held between a porous support membrane 31, which has the same diameter as the interior of the lower portion of the spin filter 1. In this variation, the support membrane 31 is retained in place by the shoulder formed by the reduced diameter of the bottom 13 of the device. The filter 29 may be fixed against the support membrane 31 by a retaining ring 33 which fits securely against the inner wall of the lower portion of the filter column 1. The present invention is not limited to the previous illustration. It will be apparent to those skilled with previously known filter columns to provide other means of retaining the filter within a filter column. An example of a filter for use with the invention includes a borosilicate glass fiber filter. The device may also contain filters of other types such as polymeric membranes, and may also contain other functional groups for purification of the nucleic acid such as ion exchange groups or groups which would specifically bind nucleic acid sequences. Another useful material for the porous substrate is a sintered polyethylene or polypropylene as supplied by Porex of Fairbum, Ga. or GenPore of Reading, Pa. In some variations of the invention it is desirable that the porous substrate is comprised of a hydrophobic material in order to minimize holdup of the aqueous solution. It was found that pore sizes in the range of 10 micron to 150 microns worked well. The primary function of the porous material is support for the filter. It is possible to have the porous support as integral to the device. The porous support can also be in the form of an open grating.

Figure 4:
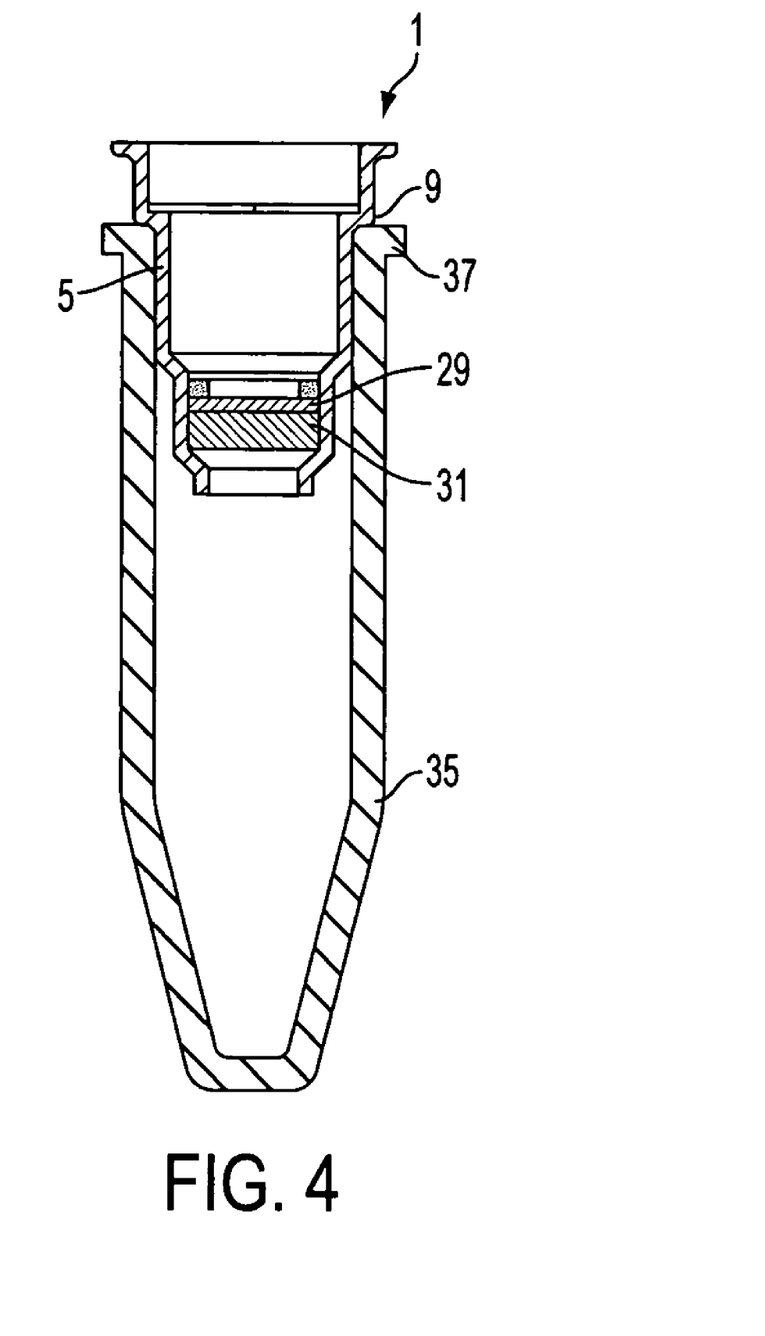
FIG. 4 illustrates a sectional view of a filter column of the present invention removably seated in a first collection tube.

FIG. 4 illustrates a variation of a filter column 1 of the present invention that is mated with a standard collection tube 35 of a first size (e.g., a 1.5 mL tube.) Standard collection tubes contain an integral body made of polymers such as polypropylene and have a standard inner diameter. As shown in FIG. 4, the second body portion 5 of the filter column 1 may fit securely against an inner walls of the collection tube 35. The first bearing surface 9 may rest against a shoulder formed by a rim 37 of the collection tube 35. Accordingly, when the tube 35 and filter column 1 spin in the centrifuge, liquid placed into the filter column 1 is forced through a filter 29 and collects in the collection tube 35. In this variation, the sizing of the first body portion 5 along with the bearing surface 9 permits stable placement of the filter column 1 within in the collection tube 35. After centrifugation, the filter column can be easily removed from the used collection tube, and placed into a new collection tube or placed back into the original tube.

Figure 5:
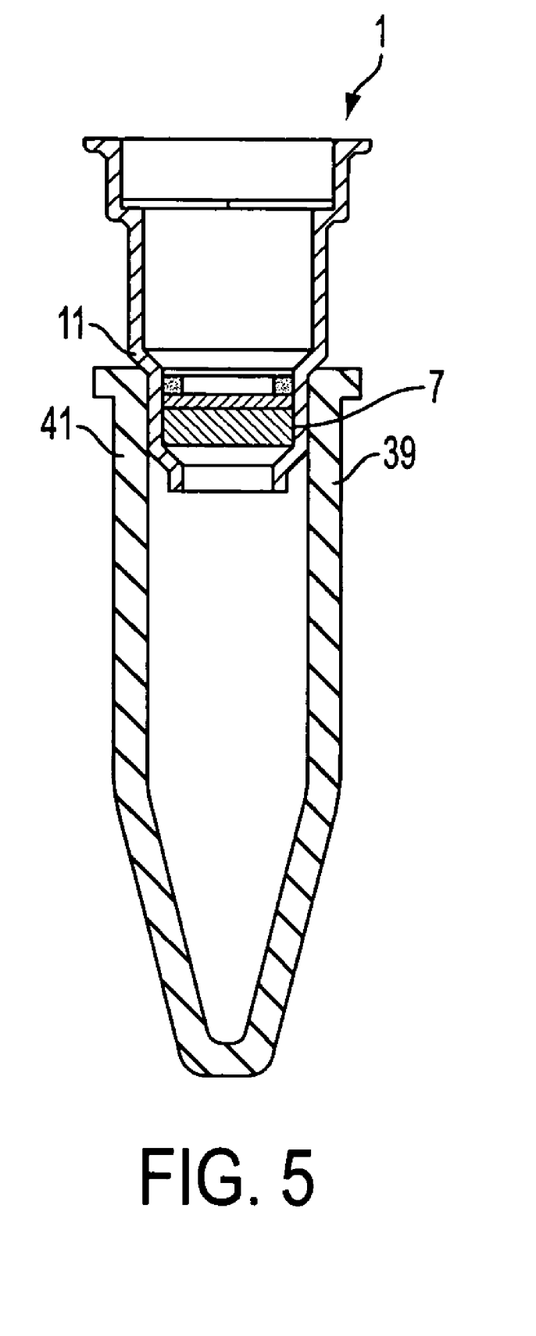
FIG. 5 illustrates a sectional view of the filter column illustrated in FIG. 4 removably seated in a second collection tube being of a different size than the first collection tube of FIG. 4.

FIG. 5 illustrates the filter column 1 of FIG. 4 placed within a collection tube 39 (e.g., a 0.5 mL tube) that is smaller than the tube illustrated in FIG. 4. As illustrated in FIG. 5, the third body portion 7 of the filter column 1 fits securely into the inner walls of the collection tube 39. During centrifugation, a bearing surface 11 of the filter column 1 seats against a rim 41 of the collection tube 39.

Figure 6A:
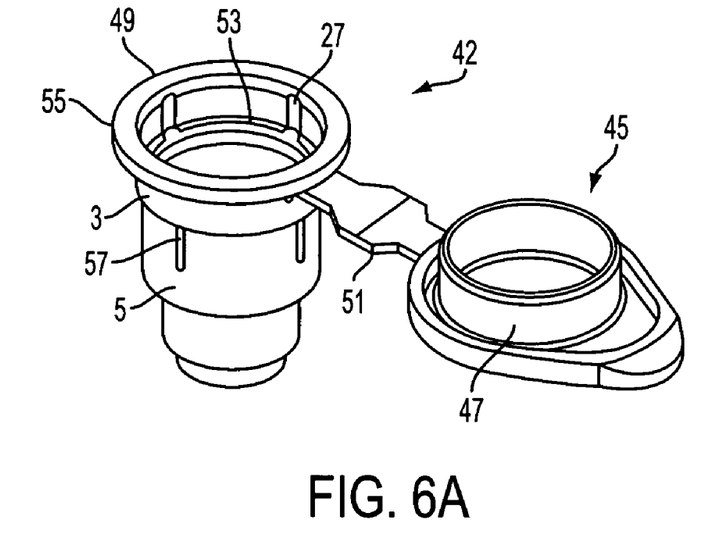
FIGS. 6A and 6B illustrate additional aspects of the invention that may be combined with any variation of the invention singly or in combination.

FIG. 6A shows another variation of a filter column 42 of the present invention having features which may be applied to any variation of the invention disclosed herein. In this variation the filter column 42 includes a lid 45 having a portion 47 which may be removably secured within a first end 49 of the filter column 42. The lid 45 may assist in preventing contamination of the filter column 42 and any solutions loaded therein. As shown, this variation of the filter column 42 contains a vent 27. Although this variation depicts the lid 45 as being integral with the filter column 42 via a hinge 51, the invention is not limited as such. For example, the present invention also contemplates a lid as being discrete from a filter column.

As illustrated in FIG. 6A, the variation of the inventive filter column 42 also may include one or more snap-fit beads or ridges 53 to assist in retention of a lid 45. In this variation the ridge 53 is included in the in a portion of a passageway in a first body portion 3 of the filter column 42. As depicted in FIG. 6A, the lid 45 and hinge 51 may be attached to the underside of an outer rim 55 (e.g., subflush to the rim 55) of the filter column 42. This placement allows the outer rim 55 to be mated to other devices as required. (e.g., a EtracSure™ sample extraction device useful for laser capture microdissection supplied by Arcturus Engineering of Mountain View, Calif.)

Another aspect of the invention depicted in FIG. 6A is deformable ribs 57 which may be located along an outside surface of the filter column 42. The deformable ribs 57 assist in securing the filter column 42 in a slightly larger diameter tube (e.g., a 2.0 mL tube) by increasing a diameter of the filter column 42. Accordingly, these ribs deform upon insertion of the filter column 42 into a tube having a diameter slightly larger than the corresponding body portion upon which the ribs 57 are situated. The number and design of the deformation ribs 57 may vary as needed, however, the ribs should be placed on a portion of the filter column that accommodates the varying sizes of tubes. The invention also contemplates deformation ribs 57 which are either plastically or elastically deformable, or exhibit a limited degree of plastic or elastic deformation.

Figure 6B:
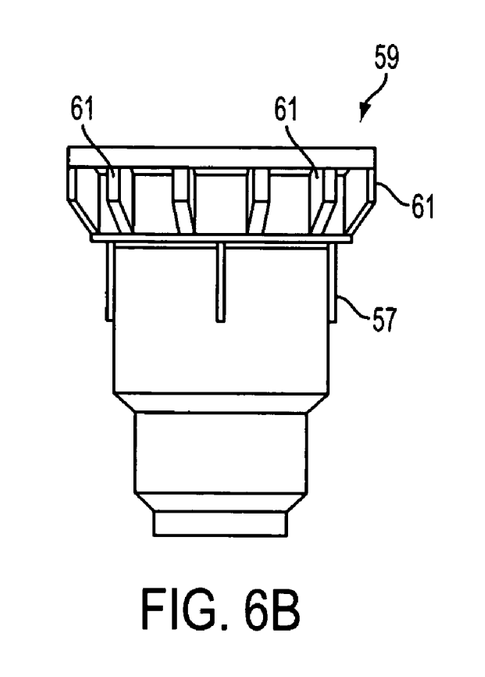

FIG. 6B illustrates another aspect of the invention in which a filter column 59 contains at least one protrusion 61 which extends radially away from the filter column 59. Such protrusions 61 may serve as "finger grips" to increase the ease with which the filter column 59 may be manipulated.

Figure 7:
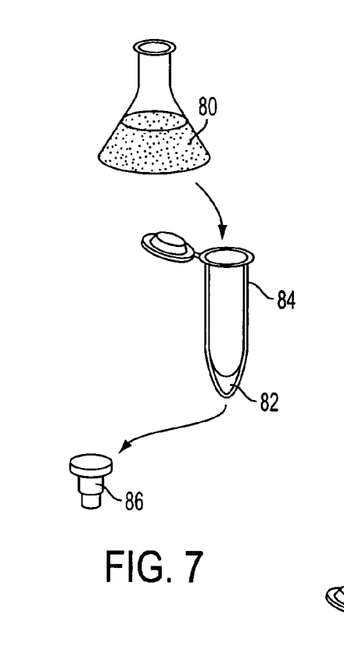
FIGS. 7, 8 and 9 illustrate a method of the present invention.
Figure 8:
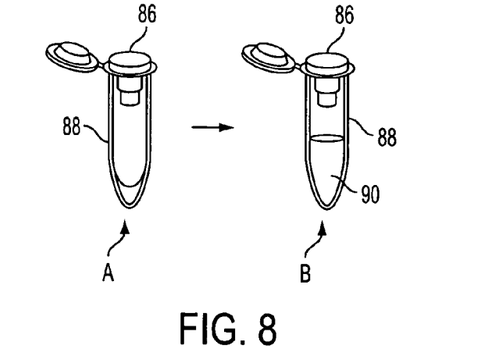
Figure 9:
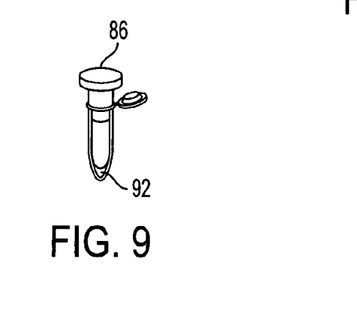

FIGS. 7-9 represent a flow diagram illustrating isolation of nucleic acids such as DNA or RNA from a biological material 80 using a filter column of the present invention. FIG. 7 represents the first step of placing a lysate 82 of biological material 80 in a collection tube 84. This lysate 82 is spun to remove large lytic debris, and the "cleared" lysate is then applied to the top of a filter column 86 of the present invention.

Alternatively, the nucleic acid containing solution does not have to come directly from lysis of biological materials. This method can also purify nucleic acids following nucleic acid amplification, enzymatic restriction digestion, ligation, extension and virtually any solution containing significant nucleic acids.

Where small amounts of nucleic acid solutions are used, it is desirable to pre-wet the filter column with binding buffer before applying the nucleic acid solution.

FIG. 8A illustrates the solution passing though a filter of the filter column 86 after centrifugation, during which the nucleic acids bind to the filter. The flow-through solution (from which the nucleotides have been mostly extracted) is retained at the bottom of a collection tube 88. Generally, tubes 82, 84 are discarded after use. Upon removal of the filter column 86 from the tube 88, the binding buffer (flow through) is discarded, and the filter column is replaced in a collection tube (either a new tube or the same tube). FIG. 8B represents repeated washing of the filter column 86 with a washing buffer and centrifuging after each addition of washing solution into the top of the filter column. Once again the flow-through accumulated at the bottom of the tube 88 is discarded. FIG. 9 represents the last step of transferring the filter column 86 of the present invention into a smaller 0.5 mL tube 92 and the addition of a small volume of elution buffer into the filter column 86. As a result of the addition of the elution buffer, the nucleic acids release from the filter into the elution buffer which is centrifuged into the bottom of the 0.5 mL tube 92. As shown in FIGS. 7-9, the inventive filter column permits use of more than one collection tube.

All of the centrifugation steps can take place in a standard bench-top microcentrifuge (for example, Eppendorf 5415C), usually at accelerations less than 20,000 g.

Figure 10:
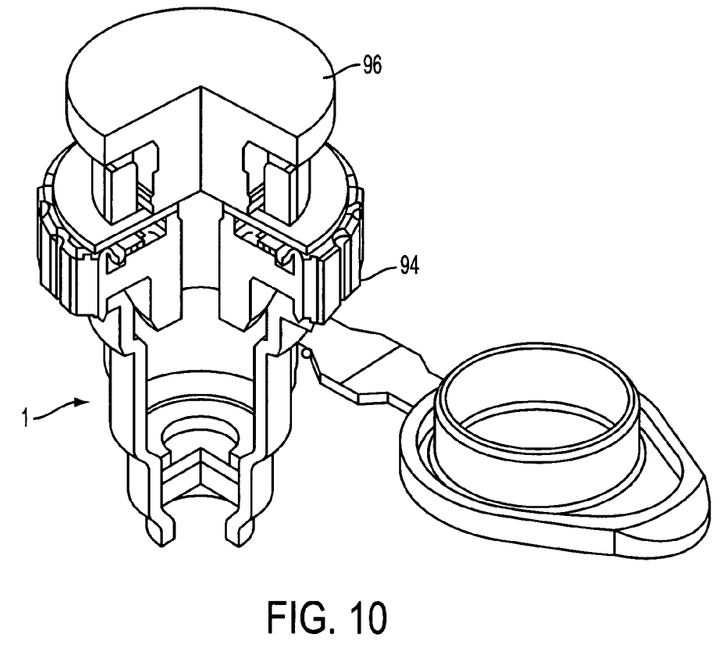
FIG. 10 illustrates a filter column of the present invention for use with a laser capture microdissection device.

The biological material used with the filter column may also be provided by laser capture microdissection extraction device as described in U.S. patent application Ser. No. 09/844,187, entitled "LASER CAPTURE MICRODISSECTION (LCM) EXTRACTION DEVICE AND DEVICE CARRIER, AND METHOD FOR POST-LCM FLUID PROCESSING," the entirety of which is hereby incorporated by reference. As shown in FIG. 10, a filter column 1 attached to a LCM extraction device flange interface 94 which seats a laser capture microdissection extraction device 96. The biological material will be located on a bottom surface of the extraction device 96.

While the present invention has been described with reference to one or more particular variations, those skilled in the art will recognize that many changes may be made thereto without departing from the spirit and scope of the present invention. Each of these embodiments and obvious various thereof are contemplated as falling within the spirit and scope of the claimed invention, which is set forth in the claims.

We claim:

1. A filter column comprising:
    a body having a passageway extending therethrough, said body comprising at least a first body portion, a second body portion, and a third body portion, where an outer diameter of said first body portion is greater than an outer diameter of said second body portion, and where said outer diameter of said second body portion is greater than an outer diameter of said third body portion;
    a filter located within said passageway, said filter adapted to isolate nucleic acids from a liquid sample;
    a first bearing surface adapted to rest against the rim of a first collection tube, where an outer diameter of the body portion directly below the first bearing surface is adapted to fit securely with the first collection tube; and
    a second bearing surface adapted to rest against the rim of a second collection tube, where an outer diameter of the body portion directly below the second bearing surface is adapted to fit securely with the second collection tube, and where the opening of the first collection tube is greater than the opening of the second collection tube;
    wherein said body is adapted to seat a laser microdissection extraction device at the first body portion.

2. The filter column of claim 1, wherein an inner diameter of said passageway in said first body portion is greater than an inner diameter of said passageway in said second body portion.

3. The filter column of claim 1, wherein an inner diameter of said passageway in said second body portion is greater than an inner diameter of said passageway in said third body portion.

4. The filter column of claim 1, wherein said filter is located within a portion of said passageway in said second body portion.

5. The filter column of claim 1, wherein said filter is located within a portion of said passageway in said third body portion.

6. The filter column of claim 1, further comprising a lid having a portion adapted to be removably seated within a first end of said body.

7. The filter column of claim 6, wherein said first body portion has an annular lip adapted to removably secure said lid portion in a closed position in said first end of said body.

8. A filter column for use with collection tubes of different sizes to isolate nucleic acids from a liquid sample, said filter colunm comprising:
    a body having a passageway extending therethrough, said body comprising at least a first body portion, a second body portion, and a third body portion, where an outer diameter of said first body portion is greater than an outer diameter of said second body portion, and where said outer diameter of said second body portion is greater than an outer diameter of said third body portion;
    a filter located within said passageway, said filter adapted to isolate nucleic acids from said liquid sample; and
    a plurality of bearing surfaces on an outer surface of said body, at least two of said bearing surfaces being adapted to seat on at least two of the collection tubes, each of the collection tubes having differently-sized openings, said plurality of bearing surfaces including at least a first bearing surface located between said first and second body portions, and a second bearing surface located between said second and third body portions;
    a lid having a portion adapted to be removably seated within a first end of said body; and at least one vent disposed on an interior wall of said body and adjacent to said first end of said body, wherein said vent is in fluid communication with an exterior of said filter column as said lid is adapted to be removably seated within said first end of said body;
    wherein said first end of said body is adapted to seat a laser microdissection extraction device.

9. The filter column of claim 8, comprising four vents.

10. The filter colunm of claim 6, wherein said lid includes a hinge being integral to said body.

11. The filter column of claim 10, wherein said hinge is offset to said first end of said body.

12. The filter column of claim 1, further comprising deformable ribs protruding from an outside surface of said body.

13. The filter column of claim 1, further comprising a plurality of protrusions on said body and extending radially away from said body.

14. The filter column of claim 1, wherein said outer diameter of said second body portion is selected such that said body is removably locatable within a 1.5-2.0 ml centrifuge tube.

15. The filter column of claim 1, wherein each of said bearing surfaces is adapted to seat on respective collection tubes of different sizes.

16. The filter column of claim 1, wherein said outer diameter of said second body portion is between 0.32 and 0.37 in.

17. The filter colunm of claim 1, wherein said outer diameter of said third body portion is selected such that said body is removably locatable within a 0.5 mL centrifuge tube.

18. The filter column of claim 1, wherein said outer diameter of said third body portion is between 0.25 and 0.27 in.

19. The filter column of claim 1, further comprising a fourth body portion and a third bearing surface wherein an outer diameter of said fourth body portion is less than an outer diameter of said third body portion.

20. The filter column of claim 1, having a microliter capacity of greater than 200 microliters, having a filter area of greater than 1,000 mm$^2$ and having a height from a top of said body to a top of said second bearing surface being less than 0.5 in.

21. A filter column for use with collection tubes of different sizes to isolate nucleic acids from a liquid sample, said filter column comprising:
   a body having a passageway extending therethrough, said body comprising at least a first body portion, a second body portion, and a third body portion, where an outer diameter of said first body portion is greater than an outer diameter of said second body portion, and where said outer diameter of said second body portion is greater than an outer diameter of said third body portion;
   a filter located within said passageway, said filter adapted to isolate nucleic acids from said liquid sample; and
   a plurality of bearing surfaces on an outer surface of said body, at least two of said bearing surfaces being adapted to seat on at least two of the collection tubes, each of the collection tubes having differently-sized openings, said plurality of bearing surfaces including at least a first bearing surface located between said first and second body portions, and a second bearing surface located between said second and third body portions;
   wherein a first end of said body is adapted to seat a laser microdissection extraction device.

22. The filter column of claim 21, wherein said laser microdissection extraction device is adapted to connect to a laser microdissection capture device.

23. A kit for isolating nucleic acids, the kit comprising: a filter column as described in any of claims 1-22; at least one collection tube; a binding buffer, containing a chaotropic agent; a washing solution; and an elution buffer.

24. The filter column of claim 1 wherein the filter column is seated on the first or second collection tube such that the filter colunm and collection tube combination is suitable for centrifugation.

25. The filtration device of claim 1 wherein the first and second bearing surfaces are located between body portions.

26. The filtration device of claim 1 wherein the first bearing surface is located between the first and second body portions, and the second bearing surface is located between the second and third body portions.

* * * * *